US010308925B2

(12) United States Patent
Tang et al.

(10) Patent No.: US 10,308,925 B2
(45) Date of Patent: Jun. 4, 2019

(54) METHIONINE LYASE, ENCODING GENE AND BIOSYNTHETIC METHOD THEREOF

(71) Applicant: Hubei University Of Technology, Wuhan, Hubei (CN)

(72) Inventors: Yajie Tang, Wuhan (CN); Kaizhi Jia, Wuhan (CN); Yanghua Xu, Wuhan (CN); Quan Zhang, Wuhan (CN); Hongmei Li, Wuhan (CN)

(73) Assignee: HUBEI UNIVERSITY OF TECHNOLOGY, Wuhan (CN)

( * ) Notice: Subject to any disclaimer, the term of this patent is extended or adjusted under 35 U.S.C. 154(b) by 29 days.

(21) Appl. No.: 15/127,903

(22) PCT Filed: Dec. 3, 2015

(86) PCT No.: PCT/CN2015/096230
§ 371 (c)(1),
(2) Date: Sep. 21, 2016

(87) PCT Pub. No.: WO2016/197561
PCT Pub. Date: Dec. 15, 2016

(65) Prior Publication Data
US 2017/0260518 A1    Sep. 14, 2017

(30) Foreign Application Priority Data
Jun. 9, 2015  (CN) .......................... 2015 1 0311606

(51) Int. Cl.
| C12N 15/70 | (2006.01) |
| C12N 15/74 | (2006.01) |
| C12N 9/88 | (2006.01) |
| C12N 15/81 | (2006.01) |
| G01N 30/50 | (2006.01) |
| G01N 30/80 | (2006.01) |
| G01N 27/447 | (2006.01) |

(52) U.S. Cl.
CPC ............... *C12N 9/88* (2013.01); *C12N 15/81* (2013.01); *C12Y 404/01011* (2013.01); *G01N 27/447* (2013.01); *G01N 30/50* (2013.01); *G01N 30/80* (2013.01)

(58) Field of Classification Search
CPC .......... C12N 9/88; C12N 15/70; C12N 15/74; C12N 1/14; C12Y 404/01001
USPC ...... 435/232, 320.1, 252.3, 254.11; 536/23.2
See application file for complete search history.

(56) References Cited

U.S. PATENT DOCUMENTS 5,888,506 A    3/1999  Tan

FOREIGN PATENT DOCUMENTS

| CN | 1174512 A | 2/1998 |
| CN | 104928310 A | 9/2015 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Chen, L. "Glarea Iozoyensis ATCC 20868 PLP-dependent transferase mRNA", GenBank, XM_008084309.1, May 22, 2014.
Tian et al. "Expression and Activities of Two Prokaryotic Expression Vectors of Eukaryotic L-methionine γ-Iyase Genes", Journal of Kunming Medical University, CN 53-1049/R, 2012, (5), 11-14.

* cited by examiner

*Primary Examiner* — Robert B Mondesi
*Assistant Examiner* — Mohammad Y Meah
(74) *Attorney, Agent, or Firm* — Birch, Stewart, Kolasch & Birch, LLP

(57) ABSTRACT

Embodiment of the present invention discloses a kind of methionine lyase and its encoding gene and biosynthetic method. According to the present invention, the gene encoding methionine lyase as shown in SEQ ID No. 1 is separated from the genome of *C. rosea*. Embodiment of the present invention further provides an efficient biosynthetic method of methionine lyase, comprising: (1) cloning gene (shown in SEQ ID No.1) encoding methionine degradation enzyme into a yeast expression vector to construct recombinant yeast expression vector; (2) transforming the recombinant yeast expression vector into *Saccharomyces cerevisiae* to obtain expression strain; (3) inducing the expression strain to express the methionine lyase, collecting induced strains, purifying expressed recombinant methionine lyase. Purity of recombinant methionine lyase prepared according to the present invention is above 90%, and its efficiency of degradating methionine can reach $0.53\pm0.0030$ μM MTL·h$^{-1}$·mg protein$^{-1}$.

13 Claims, 2 Drawing Sheets

Figure 1:
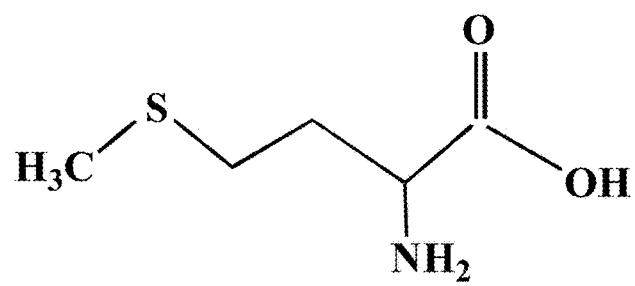

Specification includes a Sequence Listing.

Mascot Search Results

Protein View

Match to: gi|0118|STR3 Score: 448 Expect: 2.3e-043

Found in search of H:\s96r12\20100126\96\ppw_A5_142679458704.txt

Nominal mass ($M_r$): 49432; Calculated pI value: 6.17
NCBI BLAST search of gi|0118|STR3 against nr
Unformatted sequence string for pasting into other applications Fixed modifications: Carbamidomethyl (C)
Variable modifications: Oxidation (M)
Cleavage by Trypsin: cuts C-term side of KR unless next residue is P
Sequence Coverage: 56%

Matched peptides shown in Bold Red

```
  1 MSAPPPPNGD ANSSGADDKK SNPLLKRVDL DGHDLPPSPA PSSPRNGRRR
 51 YALATELVYT DSKDQYGASS IPIYQSATFK QTSASGGQAE YDYTRSGNPT
101 RTHLERHLAK IMNANKALAI SSGMGALDVI TRLLRPGDEV ITGDDLYGGT
151 HRLLTYLASN QGIIVHHVDT TDAETVKARI SDKTAMVLLE TPTNPLIKIV
201 DIPTIARNAH EANEKALVVV DNTMLSPMLL NPLDLGADIV YESGTKYLSG
251 HHDIMAGVIA VNDVEIGNKL FFTINSIGCG LSPNDSFLLM RGVKTLAIRM
301 ERQQTNAQAI AEFLESHGFR VRYPGLKSHP QVDLHWSMAR GAGAVLSFET
351 GDPTVSQRIV EAARLWAISV SFGCVNSLIS MPCQMSHASI DAKTRRERQM
401 FEDITRLCVG IEDPADLIDD LSRALVQAGA VKVTLDGFHA TGAAEEELGRT
451 PRTAK
```

Fig.4

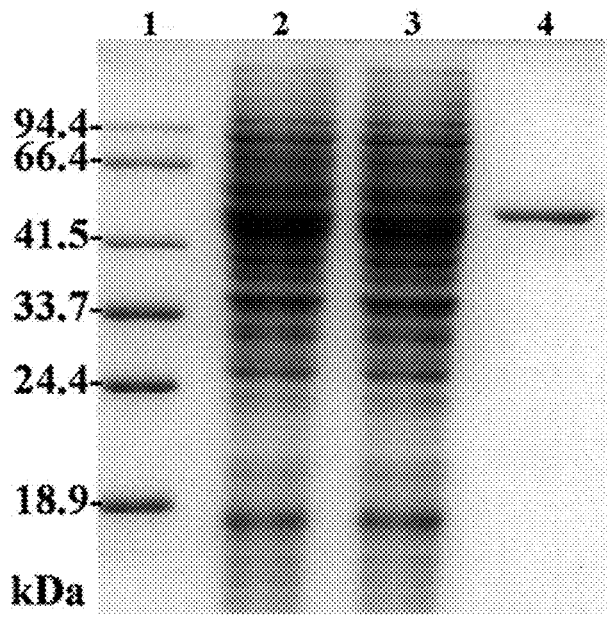

Fig.5

SEQUENCE LISTING

<160> NUMBER OF SEQ ID NOS: 4

<210> SEQ ID NO 1
<211> LENGTH: 1386
<212> TYPE: DNA
<213> ORGANISM: Artificial Sequence
<220> FEATURE:
<223> OTHER INFORMATION: Synthetic

<400> SEQUENCE: 1

```
atgtctgccc cgcctccgcc aaatggcgac gccaattcat cctccgcaga cgacaagaag      60 tcaaaccat tgctgaagcg agtcgacctc gatggacacg accttcctcc ctcaccagcc       120
ccgtctagtc cccgaaacgg acgtcgcaga tatgccctgg ccactgagct agtatacact      180
```

```
gacagcaaag atcaatatgg tgcttcgagc atccctattt accagtcagc caccttcaaa    240
cagaccagcg caagcggcgg acaggctgag tatgattaca ctcggtctgg aaatcctacc    300
cgaacccatc tagaacgcca tcttgccaag attatgaatg ccaatcgtgc cctagccatc    360
agctcgggca tgggtgcact cgacgtgatc acccgtctgc tacgaccagg tgacgaggtc    420
atcaccggcg atgatcttta cggtggtact cacagactct tgacgtatct ggcaagtaac    480
cagggaatca ttgtccatca tgtcgacacg accgacgccg agacggtcaa ggcacgcatt    540
tcggacaaga ctgctatggt cctcctcgaa acacctacaa accctcttat caagatcgtt    600
gatatcccaa caatcgcccg gaatgcccac gaagcaaatg agaaggctct tgttgttgtt    660
gataacacaa tgctctcccc aatgctgtta aaccccctcg acctcggtgc tgacatcgtt    720
tacgagtcgg gtaccaagta cctctcgggt catcacgaca tcatggctgg tgtgattgca    780
gtaaatgatg ttgagattgg taacaaacta ttcttcacta tcaattcaac tggctgcggt    840
ctgtcaccca tgactcatt ccttctcatg agaggagtca agactcttgc cattcgtatg    900
gagaagcaac agaccaatgc ccaggctatt gccgaatttc tcgagtcgca cggattccga    960
gttcgatatc ccggacttaa aagccatcct caatatgacc tacactggtc aatggcccgt   1020
ggcgctggag ctgtcctgtc cttcgaaacc ggtgacccaa cagtatccca acgaatcgtt   1080
gaggcggcaa gactgtgggc catcagcgtc agttttggat gtgtcaacag tctcattagc   1140
atgccttgcc agatgagcca tgcgagtatt gatgccaaga caagaagaga agacagatg    1200 ccggaagata tcattcgtct atgcgttggt atcgaagatc ctgctgactt gattgacgat   1260
ctgtcccgcg ctctggttca agctggtgcc gtaaaagtga cttggacgg ttttcatgcg    1320 acaggtgctg ctgaagagct tggacgaact ccacgcacag ccaaacacca ccaccaccac   1380
cactaa                                                              1386
```

<210> SEQ ID NO 2
<211> LENGTH: 461
<212> TYPE: PRT
<213> ORGANISM: Clonostachys rosea

<400> SEQUENCE: 2

Met Ser Ala Pro Pro Pro Asn Gly Asp Ala Asn Ser Ser Ser Ala
1               5                   10                  15

Asp Asp Lys Lys Ser Asn Pro Leu Leu Lys Arg Val Asp Leu Asp Gly
            20                  25                  30

His Asp Leu Pro Pro Ser Pro Ala Pro Ser Ser Pro Arg Asn Gly Arg
        35                  40                  45

Arg Arg Tyr Ala Leu Ala Thr Glu Leu Val Tyr Thr Asp Ser Lys Asp
    50                  55                  60

Gln Tyr Gly Ala Ser Ser Ile Pro Ile Tyr Gln Ser Ala Thr Phe Lys
65                  70                  75                  80

Gln Thr Ser Ala Ser Gly Gly Gln Ala Glu Tyr Asp Tyr Thr Arg Ser
                85                  90                  95

Gly Asn Pro Thr Arg Thr His Leu Glu Arg His Leu Ala Lys Ile Met
            100                 105                 110

Asn Ala Asn Arg Ala Leu Ala Ile Ser Ser Gly Met Gly Ala Leu Asp
        115                 120                 125

Val Ile Thr Arg Leu Leu Arg Pro Gly Asp Glu Val Ile Thr Gly Asp
    130                 135                 140

Asp Leu Tyr Gly Gly Thr His Arg Leu Leu Thr Tyr Leu Ala Ser Asn
145                 150                 155                 160

-continued

```
Gln Gly Ile Ile Val His His Val Asp Thr Thr Asp Ala Glu Thr Val
                165                 170                 175
Lys Ala Arg Ile Ser Asp Lys Thr Ala Met Val Leu Leu Glu Thr Pro
            180                 185                 190
Thr Asn Pro Leu Ile Lys Ile Val Asp Ile Pro Thr Ile Ala Arg Asn
        195                 200                 205
Ala His Glu Ala Asn Glu Lys Ala Leu Val Val Asp Asn Thr Met
    210                 215                 220
Leu Ser Pro Met Leu Leu Asn Pro Leu Asp Leu Gly Ala Asp Ile Val
225                 230                 235                 240
Tyr Glu Ser Gly Thr Lys Tyr Leu Ser Gly His His Asp Ile Met Ala
                245                 250                 255
Gly Val Ile Ala Val Asn Asp Val Glu Ile Gly Asn Lys Leu Phe Phe
            260                 265                 270
Thr Ile Asn Ser Thr Gly Cys Gly Leu Ser Pro Asn Asp Ser Phe Leu
        275                 280                 285
Leu Met Arg Gly Val Lys Thr Leu Ala Ile Arg Met Glu Lys Gln Gln
290                 295                 300
Thr Asn Ala Gln Ala Ile Ala Glu Phe Leu Glu Ser His Gly Phe Arg
305                 310                 315                 320
Val Arg Tyr Pro Gly Leu Lys Ser His Pro Gln Tyr Asp Leu His Trp
                325                 330                 335
Ser Met Ala Arg Gly Ala Gly Ala Val Leu Ser Phe Glu Thr Gly Asp
            340                 345                 350
Pro Thr Val Ser Gln Arg Ile Val Glu Ala Ala Arg Leu Trp Ala Ile
        355                 360                 365
Ser Val Ser Phe Gly Cys Val Asn Ser Leu Ile Ser Met Pro Cys Gln
    370                 375                 380
Met Ser His Ala Ser Ile Asp Ala Lys Thr Arg Arg Glu Arg Gln Met
385                 390                 395                 400
Pro Glu Asp Ile Ile Arg Leu Cys Val Gly Ile Glu Asp Pro Ala Asp
                405                 410                 415
Leu Ile Asp Asp Leu Ser Arg Ala Leu Val Gln Ala Gly Ala Val Lys
            420                 425                 430
Val Thr Leu Asp Gly Phe His Ala Thr Gly Ala Ala Glu Glu Leu Gly
        435                 440                 445
Arg Thr Pro Arg Thr Ala Lys His His His His His
    450                 455                 460
```

<210> SEQ ID NO 3
<211> LENGTH: 40
<212> TYPE: DNA
<213> ORGANISM: Artificial Sequence
<220> FEATURE:
<223> OTHER INFORMATION: Synthetic

<400> SEQUENCE: 3
cccaagctta acacaatgtc tgccccgcct ccgccaaatg                40

<210> SEQ ID NO 4
<211> LENGTH: 53
<212> TYPE: DNA

```
<213> ORGANISM: Artificial Sequence
<220> FEATURE:
<223> OTHER INFORMATION: Synthetic

<400> SEQUENCE: 4
cgcggatcct tagtggtggt ggtggtggtg tttggctgtg cgtggagttc gtc        53
```

METHIONINE LYASE, ENCODING GENE AND BIOSYNTHETIC METHOD THEREOF

REFERENCE TO SEQUENCE LISTING SUBMITTED VIA EFS-WEB

This application includes an electronically submitted listing in .txt format. The .txt file contains a sequence listing entitled "2017-05-26 6256-0107PUS1 ST25.txt"created on May 26, 2017 and is 6,681 bytes in size. The sequence listing contained in this .txt file is part of the specification and is hereby incorporated by reference herein in its entirety.

TECHNICAL FIELD

Embodiments of the present invention relate to methionine lyase, more particularly to methionine lyase from fungus and its encoding gene. Embodiments of the present invention further relate to a biosynthetic method for obtaining the methionine lyase, which belongs to field of methionine lyase and biosynthesisthereof.

BACKGROUND

Methionine lyase has a wide range of industrial and medical applications. In industry field, methionine lyase uses methionine as substrate to conduct direct catalytic synthesis of methyl mercaptan, and dimethyl sulfide, dimethyl disulfide and dimethyl trisulfide as its derivatives. These sulfur compounds are important food additives spices, mainly for preparation of corn, tomatoes, potatoes, milk, pineapple and orange types of fruit flavor and fragrant flavor (Martinez-Cuesta Mdel, C., Pelaez, C., Requena, T., 2013. Methionine metabolism: major pathways and enzymes involved and strategies for control and diversification of volatile sulfur compounds in cheese. Crit Rev Food Sci Nutr. 53, 366-385.); Further, main product of methyl mercaptan is also an important fuel additive, while it can be used as a precursor compound for producing methionine and insecticides (Gutierrez, O. Y, Zhong, L. S., Zhu, Y. Z., Lercher, J. A., 2013. Synthesis of methanethiol from $CS_2$ on Ni—, Co—, and K-Doped $MoS_2/SiO_2$ catalysts. Chemcatchem. 5, 3249-3259; Zhang, Y. H., Chen, S. P., Wu, M., Fang, W. P., Yang, Y. Q., 2012. Promoting effect of $SiO_2$ on the $K_2WO_4/Al_2O_3$ catalysts for methanethiol synthesis from methanol and $H_2S$. Catal Commun. 22, 48-51.).

Methionine lyase has a wide range of applications in medical field, and can be used as the enzymic preparations in cancer adjuvant therapy. By adding it to diet of cancer patient, methionine in diet can be degraded, which can reduce dependence of cancer cells to exogenous methionine, so as to achieve object of adjuvant therapy (Sun, X., Yang, Z., Li, S., Tan, Y., Zhang, N., Wang, X., Yagi, S., Yoshioka, T., Takimoto, A., Mitsushima, K., Suginaka, A., Frenkel, E. P., Hoffman, R. M., 2003. In vivo efficacy of recombinant methioninase is enhanced by the combination of polyethylene glycol conjugation and pyridoxal 5'-phosphate supplementation. Cancer Res. 63, 8377-8383.); meanwhile, methionine lyase can also get into cancer cells by way of infection, causing death and serious accumulation of the cancer cells, which is a cutting-edge technology in gene therapy for cancer (Venkatachalam, K V, 2015. Novel cancer therapy: Targeting methionine metabolism. FASEB J. 29(1): 897).

Methionine lyase is widely present in protokaryon and is not yet found in fungus. Prokaryotic methionine lyase gene is hard to be expressed efficiently in eukaryotic fermentation microorganism due to codon bias problem, which restricts capability improvement of the eukaryotic microorganisms, especially some food-related fermentation microorganisms. In addition, using prokaryotic methionine lyase for cancer treatment is likely to cause immune reaction (El-Sayed, A S, 2010. Microbial L-methioninase: Production, molecular characterization, and therapeutic applications Appl Microbiol Biotechnol 86, 445-467.). Accordingly, providing methionine lyase with eukaryotic source becomes main way to overcome above problems.

SUMMARY OF INVENTION

An object of the present invention is to provide methionine lyase from fungus;

Second object of the present invention is to provide encoding gene of methionine lyase from fungus;

Another object of the present invention is to provide a biosynthetic method of methionine lyase.

The objects of the present invention are realized by solutions as below.

A gene encoding methionine lyase, cDNA sequence of which is (a), (b) or (c) as follows:

(a) nucleotide as shown in SEQ ID No. 1;
(b) nucleotide which is capable of being hybridized with complementary sequence of SEQ ID NO: 1 in strict hybridization condition;
(c) nucleotide sequence with homology of at least 80% to the nucleotide sequence as shown in SEQ ID No. 1; preferably, nucleotide sequence with homology of at least 90% to the nucleotide sequence as shown in SEQ ID No. 1; more preferably, nucleotide sequence with homology of at least 95% to the nucleotide sequence as shown in SEQ ID No. 1; most preferably, nucleotide sequence with homology of at least 97% to the nucleotide sequence as shown in SEQ ID No. 1.

Preferably, gene encoding methionine lyase separated from fungus genome is nucleotide sequence as shown in SEQ ID No. 1. The gene sequence is obtained by cloning with the genome of *C. rosea* as template, based on conservation of amino acid sequence and codon degeneracy. By NCBI Blast, consistency of amino acid sequence thereof with homologous gene reached 78%.

The wording of "strict hybridization conditions" mentioned in the present invention refers to the conditions of low ionic strength and high temperature in the field. Generally, under strict conditions, detectable degree of hybridization between the probe and its target sequence is higher than that of the other sequences (for example, at least 2 times of background). Strict hybridization conditions are sequence dependent and will be different in different environmental conditions, in which longer sequence is subjected to specific hybridization at higher temperature. The target sequence with 100% complementary with the probe can be identified, by controlling the strictness of hybridization or washing condition. Detailed guidance for nucleic acid hybridization can refer to the relevant literature as Tijssen, *Techniques in Biochemistry and Molecular Biology-Hybridization with Nucleic Probes*, "Overview of principles of hybridization and the strategy of nucleic acid assays. 1993. More specifically, the strict conditions are usually chosen to lower than the thermal melting point (Tin) of the specific sequence under the specified ionic strength pH by 5-10° C. is temperature of probe with 50% complementary to target when hybridized to the target sequence under equilibrium condition (under specified ionic strength, pH, and concentration of nucleic acid) (because of the excessive presence of target sequence, 50% of probe is occupied under $T_m$ and equilibrium condition). Strict conditions can be followed: wherein salt concentration is below about 1.0 M sodium ion concentration under pH 7.0 to 8.3, it is usually about 0.01 to 1.0 M sodium ion concentration (or other salt); and temperature for short probe (including (but not limited to) 10 to 50 nucleotides) is at least about 30° C., and temperature for long probe (including (but not limited to) more than 50 nucleotides) is at least about 60° C. Strict conditions can also be achieved by adding destabilizer such as formamide. For selective or specific hybridization, the positive signal can be at least two times of background hybridization, and can be 10 times of the background hybridization depending on case. Exemplary conditions of strict hybridization can be as follows: 50% formamide, 5×SSc and 1% SDS, culturing at 42° C.; or 5×SSC, 1% SDS, culturing at 65° C., washing in 0.2×SSc, and washing at 65° C. in 0.1% SDS. The washing can be carried out for 5, 15, 30, 60, 120 minutes or more.

The wording of "multiple" in context usually means number of 2 to 8, preferably 2 to 4, which depends on position of amino acid residues in three-dimensional structure or type of amino acid; the wording of "replace" refers to substitute one or more amino acid residues with different amino acid residues respectively; the wording of "missing" is refers to reduction of number of the amino acid residues, that is, lacking one or more amino acid residues; the wording of "insert" refers to change of the amino acid residues sequence relative to natural molecules, wherein the change causes addition of one or more amino acid residues.

Embodiment of the present invention further provides methionine degradation enzyme, the amino acid sequence of which is as shown in SEQ ID No. 2.

The recombinant expression vector of methionine lyase gene is surely included in protection scope of the present invention. Preferably, the recombinant expression vector is recombinant yeast expression vector.

Further, recombinant host cell containing the recombinant expression vector also belongs to protective technical solution of the present invention. Preferably, the recombinant host cell is a recombinant *Saccharomyces cerevisiae* cell.

Another object of the present invention is to provide a biosynthetic method of methionine lyase, comprising steps of:
(1) cloning methionine degradation enzyme gene as shown in SEQ ID No. 1 into a yeast expression vector to construct recombinant yeast expression vector expressing the methionine degradation enzyme;
(2) transforming the constructed recombinant yeast expression vector expressing the methionine degradation enzyme into *Saccharomyces cerevisiae* to obtain expression strain of methionine lyase;
(3) inducing the expression strain of methionine lyase to express the methionine lyase, collecting induced expressing strain which is then broken, and purifying expressed recombinant methionine lyase.

In order to achieve better expression effect, preferably, in the step (1), the nucleotide as shown in SEQ ID No. 1 was directionally cloned into a yeast expression vector pYES2 by double enzyme digest of HindIII and BamHI, to obtain recombinant yeast expression vector pYES2-STR3 overexpressing the methionine degradation enzyme;
wherein the recombinant yeast expression vector pYES2 is constructed by step of: taking genome of the black truffle spore as a template, taking SEQ ID No. 3 as a upstream primer and SEQ ID No. 4 as a downstream primer to amplify gene encoding methionine degradation enzyme, which is cloned into the expression vector pYES2, to obtain the recombinant yeast expression vector pYES2-STR3; wherein the *Saccharomyces cerevisiae* in step (2) is *Saccharomyces cerevisiae* INVSc1;
wherein manner of inducing the expression strain of methionine lyase to express the methionine lyase in step (3) is preferably to induce the expression strain of the methionine lyase to express the methionine lyase by galactose;
wherein conditions of inducing are preferably as follows: OD600 before induction is 0.4, concentration of the galactose was 2% (w/v), inducing expression temperature is 30° C., inducting time was 16 hours.

The purifying in the step (3) comprises steps of: cleaning and regenerating HisTrap FF Ni—column, column equilibration being conducted with column equilibration buffer; after the equilibration is completed, collected strain after induced expression being resuspended by the column equilibration buffer, then being sonicated, then being centrifuged to get supernatant for loading and binding; after loading is completed, washing away non-specific impurities on column by using elution buffer containing 20 mM of imidazole; collecting target protein with elution buffer containing 200 mM imidazole; purifying and collecting the collected target protein through desalting column to obtain purified methionine-degradating enzyme.

Components of the column equilibration buffer are: 20 mM Tris-HCl pH=8.5, 300 mM KCl, 10 mM imidazole, 10% glycerol, 1 mM PMSF; components of elution buffer are: 20 mM Tris-HCl pH=8.5, 300 mM KCl, 20 mM imidazole, 10% glycerol, 1 mM PMSF.

Compared with the prior art, embodiment of the present invention has the following advantages and effects: by optimizing the gene sequence and expression vector and expression conditions, purity of the obtained methionine lyase STR3 reaches 90% or above, efficiency of methionine degradation is 0.53±0.0030 μM MTL·$h^{-1}$·mg protein$^{-1}$. At present, there is no report on direct degradation of methionine, and transamination product KMBA thereof (synthesizing methyl mercaptan), in eucaryon.

Definition of Terms in the Present Invention

All technical and scientific terms used in this article will have the same meaning as those of the general technical staff in the field of the present invention, unless otherwise defined. Although any method, apparatus, and material may be used in the practice or test of the present invention to be similar or equivalent to those described herein, the preferred method, apparatus, and material are described.

Term "recombinant host cell line" or "host cells" means cells containing the polynucleotides of the present invention, no matter what method is used to insert to produce the recombinant host cells, such as direct uptake, transduction, f-paired or other methods known in the field. Host cells can be the primary cell or eukaryotic cell, and the host cell can also be a single leaf or double leaf plant cell.

The term "nucleotide" means single stranded and double stranded forms of deoxyribonucleotides, deoxidation ribonucleoside, ribonucleoside or ribonucleotide and polymers thereof. Unless specific restricted, the term covers nucleic acids containing known analogs of natural nucleotide, in which the analogs is with binding properties similar to reference nucleic acid, and metabolism similar to naturally produced nucleotide. Unless otherwise specified, the term also refers to oligonucleotide analogue, including PNA (peptide nucleic acid), a DNA analogue (such as a phosphate ester, phosphate ester, etc) used in antisense technology. Unless otherwise specified, the specific nucleic acid sequences also implicitly cover their conservatively modified variants (including (but not limited to) degenerate codon substitution) and complementary sequences as well as explicitly specified sequences. In particular, the degenerate codon substitution can be realized by producing a sequence with third position of one or more selected (or all) codon substituted by mixed basic group and/or deoxyinosine residues (Batzer et al, Nucleic Acid Res. 19:5081 (1991); Ohtsuka et al, J. Biol. Chem. 260:2605-2608 (1985); 與 Cassol et al, (1992); Rossolini et al, Mol Cell. Probes 8:91-98 (1994)).

The term "polypeptide", "enzyme" and "protein" are interchangeably used in context to refer to the polymer of the amino acid residue. That is, the description of the polypeptide also applies to the description of the peptide and the description of the protein, and vice versa. The term applies to a naturally produced amino acid polymer, and amino acid polymer with one or more amino acid residues being non-naturally encoded amino acids. As used in context, the term covers any length of chains of amino acids, including a full-length protein (antigen), in which amino acid residues is connected via a covalent peptide bond.

BRIEF DESCRIPTION OF ACCOMPANYING FIGURES

Figure 2:
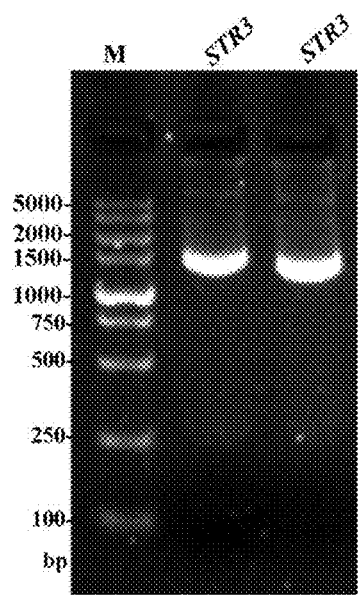
Figure 3:
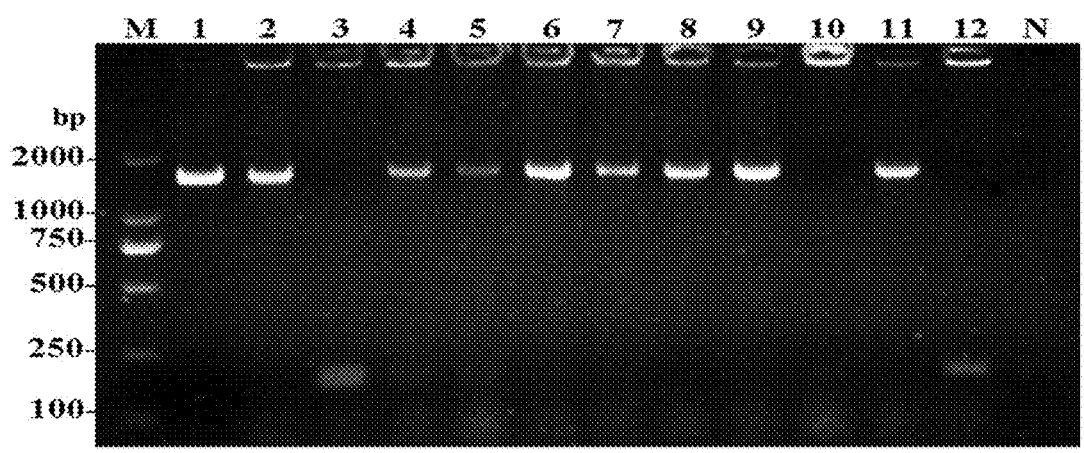

FIG. 1 shows a chemical structure of methionine.
FIG. 2 shows agarose gel electrophoresis of a PCR amplification for encoding methionine lyase gene; the M is DL5000.
FIG. 3 shows PCR screening pYES2-STR3 positive monoclonal agarose gel electrophoresis; M is DL2000, N is the negative control with water, the others are positive clone screening results.
FIG. 4 shows mass spectrometry result of methionine lyase.
FIG. 5 is a SDS-PAGE diagram of expressing and purifying methionine degradation enzyme STR3 under optimized conditions; 1: Marker, 2: supernatant obtained by cell disruption and centrifugation, 3: fluid wear (a protein mixture liquid flows through uncombined part of combining column), 4: STR3 after Nickel column purified.

EMBODIMENTS

Combined with the specific examples to further describe the invention, the advantages and characteristics of the invention will be more clear with the description. But these examples are only exemplary, and do not limit the scope of the present invention. Technicians in this field should be understood, in, without departing from the spirit and scope of the invention can to modify or replace the details and the form of the technical scheme of the invention, but these modifications, and alternatives are falling into the scope of protection of the invention.

1. Experimental Materials

*Clonostachys rosea* (isolated and stored in the inventors' laboratory, GeneBank accession number KT007105);
*Saccharomyces cerevisiae* INVSc1 and expression plasmid pYES2 are purchased from Invitrogen Corporation (Improved method for high efficiency transformation of intact yeast cells Nucleic Acids Res 1992, 20: . . . 1425).
Embodiment 1: Cloning and Expression Vector Construction of Methionine Lyase Gene STR3

(1) Based on the amino acid methionine lyase sequence conservation and codon degeneracy, homologous cloning the conserved sequences of methionine lyase in *C. rosea*, amplifying 5' and 3' ends of the conserved sequences by RACE technology, conducting NCBI Blast after sequence splicing, then finding its consistency in amino acid level with homologous protein in the model strain is 78%. The nucleotide sequence thereof is for example the nucleotide sequence shown in SEQ ID NO. 1, and its deduced amino acid sequence is as shown in SEQ ID NO. 2.

(2) Extraction of the expression plasmid pYES2
Taking a test tube containing culture medium of 10 mL LB (tryptone 10 g/L, yeast extract 5 g/L, NaCl 10 g/L, Ampicillin 100 mg/L) to inoculate *E. coli* Top10 containing pYES2 plasmid in the tube, culture at 37° C. and 180 rpm overnight, extracting plasmid according to a method in the plasmid kit; after plasmid extraction, marking and placing it in refrigerator at 4° C. to wait for use in next step.

(3) PCR amplification of STR3 with sequence encoding His tag.
Reaction system of PCR amplification: genome of *C rosea* 0.5 μL, 10×buffer 5 μL, dNTPs 4 μL, STR3-5' upstream primer 1 μL, STR3-3' downstream primer 1 μL, pfu polymerase 0.4 μL, plus ddH2O to 50 μL.

STR3-5' upstream primer is
5'-CCC*AAGCTT*AACACAATGTCTGCCCCGCCTCCGCCAAATG-3',

STR3-3' downstream primer is
5'-CGC*GGATCC*TTAGTGGTGGTGGTGGTGGTGTTTGGCTGTGCGTG
GAGTTCGTC-3'.

Underlined italics therein mark the enzyme cleavage site HindIII and BamHI, bold parts mark encoding His tag sequence.
PCR amplification conditions: 94° C. initial denaturation 10 min; 94° C. 30 s, 55° C. 30 s, 72° C. 2 min, 30 cycles; final extension to 72° C. 5 min.
After the PCR product STR3-His is detected correctly by agarose gel electrophoresis (FIG. 2), the PCR product was recovered by the kit.

(4) Construction and transformation of expression vector
using BamHI and HindIII double enzyme to digest the expression plasmids and PCR products, then recovering the enzyme digestion products by PCR product recovery kit, establishing enzyme-linkded system: pYES2 and STR3 mixed enzyme-digestion product in 8 μL, 10×T$_4$ DNA ligase buffer 1 μL, T$_4$ DNA ligase 1 μL; putting enzyme-linked system into constant temperature drying bath at 16° C.; after the treatment for 8 h, the enzyme-linked product being added to the *E. coli* Top10 competent cells; EP tube being reset in ice for 30 min, then put into 42° C. water bath for heat shock for 30 s, then put into ice statically for 2 min; 500 μL LB culture medium was added into each tube for cultivation in shaker for 60 min at 37° C. and 180 rpm; centrifuging at 4000 rpm for 4 min, taking 400 μL supernatant and gently mixing precipitate, plating it on LB plate containing 100 mg/L ampicillin, and cultivating in 37° C. thermostat chamber for 10-12 hours.

(5) Screening of positive clones
single colonies growing on the plate being inoculated on the LB plate containing 100 mg/L ampicillin, and cultured for 6 h at 37° C.; the colonies being selected for PCR analysis (FIG. 3); taking ddH$_2$O as negative control, the PCR product being detected by agarose gel electrophoresis. If the molecular weight of the target band amplified being about 1.4 kb, it was preliminarily proved the vector was successfully constructed.
The bacterial colonies corresponding to correct band are activated, and the bacteria are sequenced. The resulted sequence of sequencing showed that loaded STR3-His fragment length is 1386 bp, indicating that the expression vector pYES2-STR3 is constructed successfully.

Embodiment 2: Expression and purification of methionine degradation enzyme (1) Preparation of yeast competent cell saved *Saccharomyces cerevisiae* INVSc1 being activated on solid YPD culture medium, transferred for three times, and inoculated into YPD liquid culture medium for shaking culture at 30° C. and 200 rpm until $OD_{600}$=1.0; cells being collected and washed by precooled ultrapure water, and resuspended in 200 μL 1M sorbitol solution for the preparation of yeast competent cells.

YPD culture medium formula: Yeast Extract 10 g, Trypton 20 g, 121° C. high pressure sterilization for 20 min, adding 2% (w/v) glucose.

(2) Transformation of STR3 plasmid over-expression in *Saccharomyces cerevisiae*

PYES2-STR3 plasmid in *E. coli* TOP10 being extracted; the extracted plasmid being transformed into *Saccharomyces cerevisiae* in competent state and gently mixed, then added to precooled 0.2 cm electrode cup; gently tapping on the super clean bench to make the mixture flow to the bottom of the electrode cup; putting in an ice bath for 5 min; the electrode cup being placed in an electric conversion instrument at 1.5 kV, 5 mS, for exponential decay pulse conversion; quickly adding 1 mL precooled 1M sorbitol to the electrode cup; transferring the contents respectively to sterilized 1.5 mL EP tube; taking 300 uL thereof to be deposited to SC cultivate medium absent of uracil, inversion cultured for 2-3 d at 30° C., the selecting transformants growing on the plate for expanding culture.

Ingredients of SC culture medium: 0.67% yeast nitrogen base (without amino acid), 2% (glucose or cottonseed sugar).

(3) Induction of methionine degradation enzyme inoculating all activated yeast suspension in 50 ml SC liquid culture medium absent of uracil for 24 h continuous activation, taking all of bacterial liquid to inoculate in 200 mL Sc—U for 24 h continuous activation; after 4000 rpm centrifuge for 5 min, collecting the yeast to inoculate in 1 L SC induced culture medium, and adding 2% galactose to induce culture at 30° C., 200 rpm for 16 h induction; the inducted yeast being collected after centrifuged for 15 min by a high speed refrigerated centrifuge (J-26XP, Beckman) at 4° C., 4000 rpm.

(4) Purification of methionine degradation enzyme collected yeast quickly frozen in liquid nitrogen, then fully grinded, then added to 25 mL of lysis buffer for resuspending; ultrasound breaking (running for 3 seconds, stopping for 3 seconds, with 99 cycles) is conducted until the solution is in translucent state; after the end of the ultrasonic, centrifuging at 4° C. and 12000 rpm for 1 h to collect supernatant obtained after cells breaking and centrifuging.

Ni-NTE column being prepared, washed by ultra pure water for 3 times, washed with lysisi buffer for 3 times; the supernatant flowing through Ni-NTE column twice, collecting protein mixture liquid and going through uncombined part of combining column; nickel column is washed with washing buffer, removing impurity protein on a nickel column, with 3 mL each time and washing three times; target bands is eluted with eluntion buffer, to obtain purified STR3, then removing imidazole in elution buffer via desalting column.

Buffer for protein purification:

lysisi buffer, components of which are: 20 mM Tris HCl (pH=8.5), 300 mM KCl, 10 mM imidazole, 10% glycerol, 1 mM PMSF; washing buffer group components of which are: 20 mM Tris-HCl (pH=8.5), 300 mM KCl, 20 mM imidazole, 10% glycerol, 1 mM PMSF;

elution buffer, components of which are: 20 mM Tris-HCl (pH=8.5), 300 mM KCl, 200 mM imidazole, 10% glycerol, 1 mM PMSF;

(5) Yield of methionine degradation enzyme using BCA method to measure STR3 eluent concentration purified by nickel column, the concentration is 0.67 mg/L, collecting total of 9 mL protein eluent, and final quality of protein is 6.03 g; because volume of starting bacteria liquid is 1 L, calculated yield of methionine degradation enzyme being 6.03 g/L.

(6) Analysis of enzymatic properties of methionine degradation enzyme

With a methionine as a substrate to detect effect of removing thiol of SRT3, 5 mL enzymatic reaction system includes: 1 μg/mL STR3, 50 mM Tris-HCl (pH8.0), 5 μm PLP and 20 mM methionine. The enzyme catalyzed reaction system was placed under the temperature of 25° C. for 1 h, and the product of Methyl thiol was detected by gas chromatography with reference to Liu RS, et al. Metabolism of L-methionine linked to the biosynthesis of volatile organic sulfur-containing compounds during the submerged fermentation of *Tuber melanosporum*. Appl Microbiol Biotechnol 2013, 97: 9981-9992. Calculation result shows degradation efficiency of methionine prepared by embodiment of the present invention was 0.53±0.0030 μM MTL·$h^{-1}$·mg protein$^{-1}$.

The invention claimed is:

1. A cDNA sequence, said cDNA sequence being (a), (b) or (c) as follows:
   (a) the nucleotide sequence as shown in SEQ ID No.1;
   (b) the nucleotide which is capable of being hybridized with complementary sequence of SEQ ID NO: 1 in strict hybridization condition, wherein the strict condition is 50% formamide, 5 ×SSc and 1% SDS, culturing at 65° C., washing in 0.2 ×SSc, and washing at 65° C. in 0.1% SDS;
   (c) a nucleotide sequence with homology of at least 90% to the nucleotide sequence as shown in SEQ ID No.1.

2. A recombinant expression vector containing the cDNA sequence of claim 1.

3. A recombinant host cell containing the recombinant expression vector of claim 2.

4. A biosynthetic method, comprising steps of:
   (1) cloning methionine degradation enzyme, said enzyme having the cDNA sequence of claim 1, into a yeast expression vector to construct recombinant yeast expression vector expressing methionine degradation enzyme;
   (2) transforming the constructed recombinant yeast expression vector expressing the methionine degradation enzyme into *Saccharomyces cerevisiae* to obtain expression strain of methionine lyase;
   (3) inducing the expression strain of methionine lyase to express the methionine lyase, collecting induced expressing strain which is then broken, and purifying expressed recombinant methionine lyase.

5. The method of claim 4, wherein in the step (1), the nucleotide as shown in SEQ ID No.1 was directionally cloned into a yeast expression vector pYES2 by double enzyme digest of HindIII and BamHI, to obtain recombinant yeast expression vector pYES2-STR3 for over-expressing the methionine degradation enzyme;
   wherein the *Saccharomyces cerevisiae* in step (2) is *Saccharomyces cerevisiae* INVSc1;
   wherein manner of inducing the expression strain of methionine lyase to express the methionine lyase in step (3) is to induce the expression methionine lyase by galactose.

6. The method of claim 4, wherein the purifying in the step (3) comprises steps of:

cleaning and regenerating HisTrap FF Ni-column, column equilibration being conducted with column equilibration buffer;

after the equilibration is completed, collected strain after induced expression being resuspended by the column equilibration buffer, then being sonicated, then being centrifuged to get supernatant for loading and binding;

after loading is completed, washing away non-specific impurities on column by using elution buffer containing 20 mM of imidazole;

collecting target protein with elution buffer containing 200 mM imidazole;

purifying and collecting the target protein through desalting column to obtain purified methionine-degradating enzyme.

7. The method of claim 6, wherein components of the column equilibration buffer are: 20 mM Tris-HCl pH=8.5, 300 mM KCl, 10 mM imidazole, 10% glycerol, 1 mM PMSF;
   components of elution buffer are: 20 mM Tris-HCl pH=8.5, 300 mM KCl, 20 mM imidazole, 10% glycerol, 1 mM PMSF.

8. The cDNA sequence of claim 1, said cDNA sequence having homology of at least 95% with respect to the nucleotide sequence as shown in SEQ ID No.1.

9. The cDNA sequence of claim 1, said cDNA sequence having homology of at least 97% with respect to the nucleotide sequence as shown in SEQ ID No.1.

10. The cDNA sequence of claim 1, said cDNA sequence selected from (a) or (c) as follows:
    (a) the nucleotide sequence as shown in SEQ ID No.1;
    (c) the nucleotide sequence with homology of at least 90% to the nucleotide sequence as shown in SEQ ID No.1.

11. The cDNA sequence of claim 1, said cDNA encoding methionine lyase from fungus.

12. A recombinant expression vector containing the cDNA sequence of claim 1, wherein the recombinant expression vector is a recombinant yeast expression vector.

13. A recombinant host cell containing the recombinant expression vector of claim 2, wherein the recombinant host cell is a recombinant *Saccharomyces cerevisiae* cell.

* * * * *